US008613942B2

(12) United States Patent
Vogt et al.

(10) Patent No.: US 8,613,942 B2
(45) Date of Patent: Dec. 24, 2013

(54) MEDICAL SYSTEM, PULLING DEVICE AND METHOD FOR PULLING AN ACTIVE SUBSTANCE CHAIN

(75) Inventors: Sebastian Vogt, Erfurt (DE); Hubert Buechner, Reinheim (DE); Hans Boesebeck, Alzenau (DE)

(73) Assignee: Heraeus Medical GmbH, Wehrheim (DE)

( * ) Notice: Subject to any disclaimer, the term of this patent is extended or adjusted under 35 U.S.C. 154(b) by 82 days.

(21) Appl. No.: 12/815,463

(22) Filed: Jun. 15, 2010

(65) Prior Publication Data

US 2010/0318023 A1 Dec. 16, 2010

(30) Foreign Application Priority Data

Jun. 15, 2009 (DE) .......................... 10 2009 025 297

(51) Int. Cl.
*A61F 13/00* (2006.01)
(52) U.S. Cl.
USPC .... 424/422; 623/13.2; 623/23.48; 623/11.11; 623/17.11; 623/17.16; 623/23.18; 623/8; 128/898
(58) Field of Classification Search
USPC ............................... 424/422; 623/13.2, 23.48
See application file for complete search history.

(56) References Cited

U.S. PATENT DOCUMENTS

| 1,347,622 A | * | 7/1920 | Deininger | 604/61 |
| 2,659,369 A | * | 11/1953 | Lipman | 604/62 |
| 3,639,137 A | * | 2/1972 | Marinelli | 428/321.5 |
| 3,780,400 A | * | 12/1973 | Hinsperger | 24/16 PB |
| 3,846,846 A | * | 11/1974 | Fischer | 623/23.18 |
| 5,251,757 A | * | 10/1993 | Relyea et al. | 206/531 |
| 5,372,146 A | * | 12/1994 | Branch | 128/898 |
| 5,534,023 A | * | 7/1996 | Henley | 623/8 |
| 5,702,454 A | * | 12/1997 | Baumgartner | 128/898 |
| 5,958,465 A | * | 9/1999 | Klemm et al. | 425/116 |
| 6,183,768 B1 | | 2/2001 | Harle | |
| 6,299,590 B1 | | 10/2001 | Luscher et al. | |

(Continued)

FOREIGN PATENT DOCUMENTS

DE 2320373 A1 11/1974
WO 2006091744 A2 8/2006

OTHER PUBLICATIONS

Office Action issued Mar. 31, 2011 in DE Application No. 10 2009 025 297.5.

(Continued)

*Primary Examiner* — Nicholas Lucchesi
*Assistant Examiner* — Scott Medway
(74) *Attorney, Agent, or Firm* — Panitch Schwarze Belisario & Nadel LLP

(57) ABSTRACT

A medical system (10) is provided having a pulling device (20) and an active substance chain (50). The active substance chain (50) has at least two storage units (51) arranged like a chain, and at least one of the storage units (51) is loaded with a medicinal active substance. The pulling device (20) has a grip element (30) and a coupling element (40), and the coupling element (40) has at least one recess (41, 41'). In a free position (100) the active substance chain (50) is arranged separated from the pulling device (20), while in an inserted position (110) at least one of the storage units (51) is arranged form-fitting in a recess (41, 41'). The active substance chain (50) can be moved reversibly from the free position (100) into the inserted position (110).

17 Claims, 5 Drawing Sheets

(56) References Cited

U.S. PATENT DOCUMENTS

| | | | |
|---|---|---|---|
| 6,387,130 B1* | 5/2002 | Stone et al. | 623/17.16 |
| 6,616,673 B1* | 9/2003 | Stone et al. | 606/105 |
| 6,872,227 B2* | 3/2005 | Sump et al. | 623/13.2 |
| 7,682,400 B2* | 3/2010 | Zwirkoski | 623/23.48 |
| 2002/0099408 A1* | 7/2002 | Marks et al. | 606/200 |
| 2003/0028251 A1* | 2/2003 | Mathews | 623/17.16 |
| 2004/0097930 A1* | 5/2004 | Justis et al. | 606/61 |
| 2004/0249464 A1* | 12/2004 | Bindseil et al. | 623/17.16 |
| 2005/0278023 A1 | 12/2005 | Zwirkoski | |
| 2006/0271061 A1 | 11/2006 | Beyar et al. | |
| 2007/0055271 A1* | 3/2007 | Schaller | 606/90 |
| 2007/0162132 A1 | 7/2007 | Messerli | |

OTHER PUBLICATIONS

EP Search Report issued Nov. 19, 2010 in EP Application No. 10006203.3.

\* cited by examiner

MEDICAL SYSTEM, PULLING DEVICE AND METHOD FOR PULLING AN ACTIVE SUBSTANCE CHAIN

BACKGROUND OF THE INVENTION

The invention relates to a medical system having a pulling device and an active substance chain, the active substance chain having at least two storage units arranged like a chain, and at least one of the storage units is loaded with a medicinal active substance. The invention further relates to a pulling device for pulling an active substance chain loaded with a medicinal active substance.

German published patent application DE 2 320 373 A describes active substance chains, which are loaded with antibiotics and can be placed in wound cavities. Such active substance chains often comprise a PMMA plastic (polymethyl methacrylate), which is provided with incorporated antibiotics. These active substance chains are placed, for example, next to the artificial hip joint in the case of hip replacements, in order to prevent possible inflammations. However, depending on the indication, the active substance chains must be removed again after a few days to up to a few weeks. This removal, however, is sometimes very difficult, because the active substance chains are enclosed by newly formed connective tissue.

In the prior art it is known, for removal, to grip the active substance chains at a projecting end with tweezers, forceps, or a nail holder and to pull it out by hand. This frequently leads to the tearing and/or splitting of individual elements of the active substance chains. In such a case, the surgeon is forced to open the wound further, in order to then reach the rest of the active substance chain. This can introduce new infections and/or can prolong the healing process of the patient.

BRIEF SUMMARY OF THE INVENTION

The object of the present invention is to create a medical system that avoids the aforementioned disadvantages, in particular, prevents a tearing and/or splitting of the active substance chain.

To achieve this object, a medical system is proposed, in the scope of the invention, having a pulling device and an active substance chain, wherein the active substance chain has at least two storage units arranged like a chain, at least one of the storage units is loaded with a medicinal active substance, the pulling device has a grip element and a coupling element, and the coupling element has at least one recess, the active substance chain is arranged separated from the pulling device in a free position, at least one of the storage units is arranged in the recess with a positive fit (form-fitting) in an inserted position, and the active substance chain can be moved reversibly from the free position into the inserted position.

The main concept of the invention comprises a pulling device for the active substance chain wherein at least one of the storage units at least partially form-fits in a recess. In contrast to the known means used for pulling the active substance chain, the pulling device according to the invention has a recess whose size and shape is such that it grips around at least parts of the storage units of the active substance chain with a positive fit. In this way, a point load on the active substance chain is avoided. Instead, a large surface area coupling between the pulling device and the active substance chain ensures that at no point can high point forces act on the active substance chain. In the process of pulling an active substance chain from a wound, forces up to 300 N can occur.

By the form-fitting enclosure of at least one storage unit in at least one recess, it is ensured that this force is not a point force acting on a small area of the storage unit. Instead, a larger, in particular, hemispherical surface of the storage unit is enclosed by a similarly shaped area of the recess. The resulting positive fit between the storage unit and the recess ensures that the active substance chain can no longer be destroyed when it is pulled from the wound.

In order to guarantee a secure storage of the active substance chain in the inserted position in the pulling device, it has proven advantageous to form the at least one recess with a cylindrical or spherical construction. This shaping of the recess is particularly well suited to receive a spherical-shaped storage unit. Each spherical storage unit can then be slid into the recess, without the risk of an edge. Furthermore, it has been proven advantageous when a diameter of the at least one recess is greater than the diameter of a storage unit. In this way, a simple and easy insertion of the storage unit in the recess is ensured. In addition, fluids, such as blood, can deposit on the storage unit, so that a recess whose diameter corresponds exactly to that of the storage unit is not sufficient for receiving the storage unit. Advantageously, the diameter of the recess is 2% to 10% larger than the diameter of the storage unit.

To enable simple grasping of longer active substance chains, it has proven advantageous when the coupling element has a passage element, which forms a passage in the coupling element and/or the pulling device. Parts of the active substance chain can be guided through this passage element. If the surgeon thus pulls the active substance chain in the inserted position somewhat from the wound, he can unhook the storage units from the recesses. The active substance chain is then located in the free position. Now it is possible for the surgeon to thread the active substance chain through the passage element and to insert storage units that lie closer to the wound back into the recesses—thus, to move the active substance chain back into the inserted position. If such a grasping should once again be needed, the surgeon is no longer forced to transform the active substance chain into the free position. Instead, it would be sufficient to pull the storage units from the recesses and to push the coupling element over the active substance chain, such that this moves further in the direction of the wound. Then he could insert the storage units back into the recesses. Therefore, because the active substance chain runs through the passage element, the pulling device and/or the coupling element can be moved longitudinally over the active substance chain. Here, it has proven especially advantageous when the passage element is arranged between the at least one recess and the grip element and/or runs through the grip element. This enables an easy movement of the pulling device over the active substance chain.

Because the passage element is not used to transfer forces to the active substance chain, it has proven advantageous when the passage element has a diameter that is greater than the diameter of the at least one recess. The diameter of the passage element advantageously lies 10% to 15% above the diameter of the storage unit. Thus, a smooth passage of the active substance chain through the passage element is ensured. In particular, it has proven advantageous for spherical storage units when the passage element has a cylinder-like construction.

In a preferred embodiment, the pulling device has more than two recesses. An arrangement having two or three recesses arranged in a line on the coupling element is preferred. By the selection of a plurality of recesses, the force acting on an individual storage units in the inserted position is reduced proportionately. Consequently, the likelihood of splitting one of the active substance balls and/or destroying the active substance chain is further reduced.

To achieve self-locking of the storage unit in the recess, another embodiment distinguishes itself in which a central axis of the at least one recess is inclined relative to a plane spanned by the grip element and the coupling element. Here, it is especially advantageous when the central axis is inclined relative to the spanned plane in the direction of the grip element. If an active substance chain located in a body is to be pulled out, the storage unit is moved into the inserted position. Then the surgeon pulls on the grip element of the pulling device. Because the active substance chain has partially grown into the bone and/or the tissue of the patient, the surgeon must apply a force, which leads to the result that the storage unit is pulled through the inclined recess into the coupling element. A base of the recess then comes into contact with the storage unit, which is pressed against this base by the force applied during pulling. As a result, the storage unit locks the active substance chain in the recess. This has the advantage that the active substance chain can no longer suddenly jump out of the inserted position into the free position.

The self-locking of the active substance chain can be further reinforced if, in an entry region of the at least one recess, a collar-like retainer is arranged, in order to fix the storage unit in an entry region. The collar-like retainer can involve a chamfer or an undercut in the recess, which prevents the storage unit of the active substance chain from sliding and/or rolling out of the recess.

So that the storage unit lies in a cylinder-like recess with a positive fit, it has proven advantageous when a base region of the at least one recess has a hemispherical construction. The spherical storage unit comes to lie in the hemispherical base region. Consequently, a large surface area is formed in which a positive fit arises between the storage unit and the recess. Any force to be introduced from the pulling device into the active substance chain is then transmitted, if the latter is arranged in the inserted position, via this area of the direct form-fit contact between the storage unit and the recess.

Another advantageous embodiment is characterized in that the storage units are connected by a cord-like element. The cord-like element can include surgical steel wire onto which the storage units are pressed. Here, it has proven advantageous when the storage units are built from a PMMA plastic, which is pressed onto the cord-like element. In order to generate a corresponding effect, the PMMA plastic of the storage units is previously loaded with a medicinal active substance, such as an antibiotic.

Another advantageous embodiment of the medical system according to the invention distinguishes itself in that the coupling element has at least one slot-like connection element, wherein, in the inserted position, the connection element stores the cord-like element of the active substance chain. In one embodiment, the slot-like connection element can be arranged as a cutout in the coupling element. This makes it possible that, in the inserted position, the active substance chain can be laid in the recesses. The cord-like element is arranged in the connection element so that the active substance chain projects from one end of the coupling element. By this arrangement the coupling element can be arranged in a line with the active substance chain to be pulled, which allows a simple introduction of force into the active substance chain. Another embodiment distinguishes itself in that the connection element at least in some regions connects two recesses to each other and/or the connection element at least in some regions connects the passage element and at least one recess to each other. With this embodiment the connection element ensures that a storage unit can be stored in each of the recesses, wherein the cord-like element can run on the shortest path between the two storage units. Thus, a uniform introduction of force to the active substance chain is possible.

Another advantageous embodiment distinguishes itself in that the grip element and the coupling element are one piece, preferably integral, in particular, materially uniform, in particular, the grip element and the coupling element are arranged like a T relative to each other. The pulling device can be produced either from metal, as for example from surgical steel, or also from typical plastics, as for example PMMA, polyethylene, polypropylene, polyamide, polyetherketone and polysulfone. The shaping can be performed by casting, injection molding, or even by conventional metal processing methods, as for example forging and milling.

The object cited above is also achieved by a pulling device for pulling an active substance chain loaded with a medicinal active substance, wherein the pulling device has a grip element and a coupling element, the coupling element has, in order to pull the active substance chain, at least one recess, in which the active substance chain to be pulled can be arranged with a positive fit in an inserted position. Features and details, which were described here in connection with the medical system also obviously apply to the pulling device according to the invention, and vice versa.

In the scope of the patent application, a use of a pulling device for removing an active substance chain loaded with medicinal active substances is likewise claimed. Here, the pulling device is equipped according to the embodiments made above. Each feature and detail, which is set forth in connection with the pulling device or the medical system according to the invention, also applies to the use of the pulling device.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. Shown in the drawings are.

DETAILED DESCRIPTION OF THE INVENTION

Figure 1:
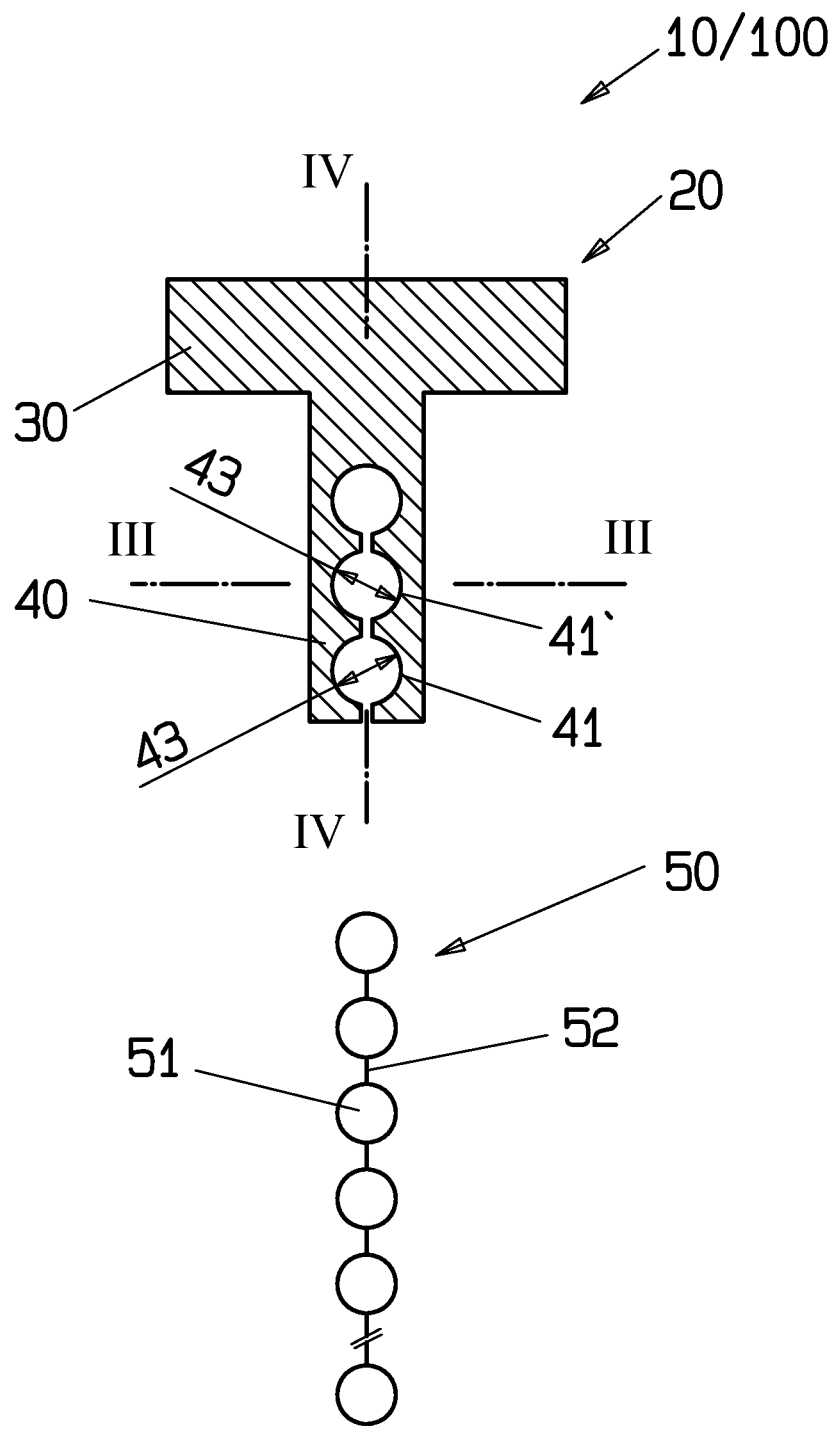
FIG. 1 is a schematic longitudinal view of a medical system according to an embodiment of the invention with the pulling device shown in sectional view and the active substance chain shown in a free position.

In FIG. 1 an embodiment of a medical system 10 is shown, which achieves the object cited above. The medical system 10 has a pulling device 20 and an active substance chain 50. The active substance chain 50 comprises an arrangement of storage units 51 lined up relative to each other like a chain, which are made of PMMA (polymethyl methacrylate) in the illustrated embodiment. These storage units 51 have been pressed onto the cord-like element 52. For the cord-like element 52 a steel wire is used. The storage units 51 are loaded with a medicinal active substance.

Active substance chains 50 configured in this way are used as active substance carriers, which are used for fighting bone tissue infections. For this purpose, they are laid directly into the infected tissue that was previously reconstructed surgically. Through the direct contact of the active substance chain 50 with the connective tissue and/or the bone tissue, the medicinal active substances can penetrate directly into this tissue. However, active substance chains 50 constructed in this way must be removed from the wound again after some time. In the prior art forceps are preferably used for this purpose but, of course, lead to the result that the active substance chains 50 are partially torn.

Figure 2:
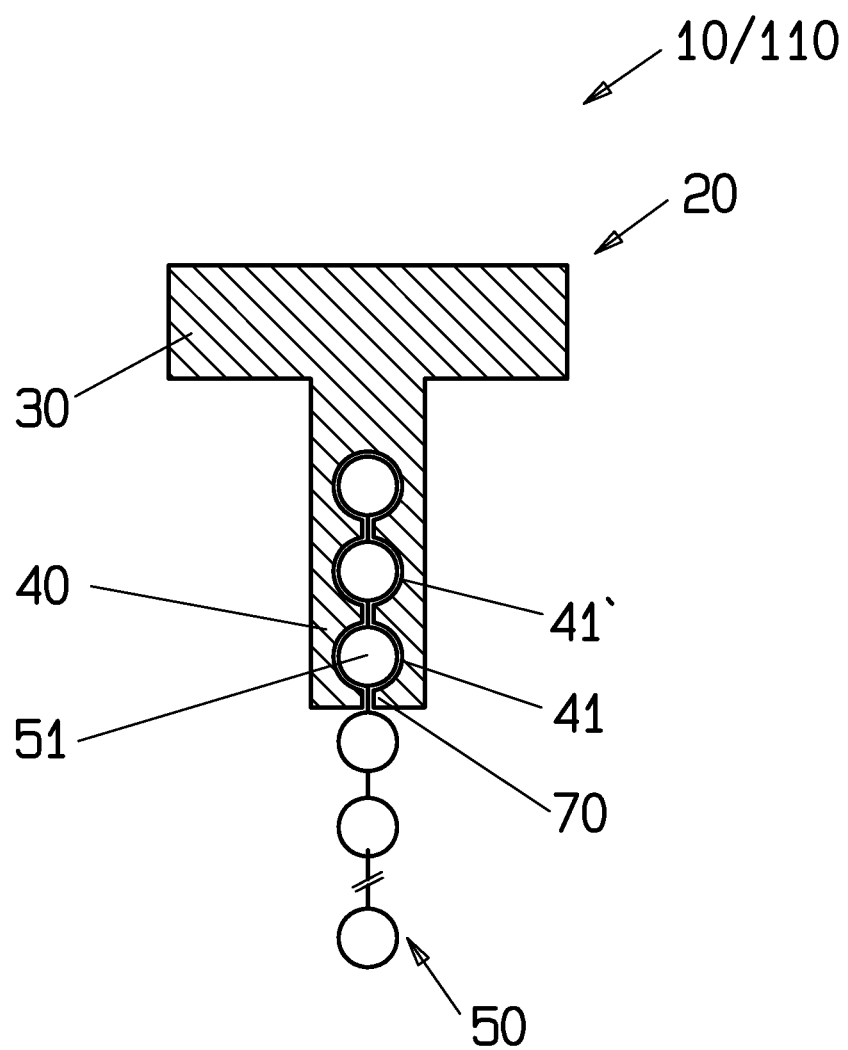
FIG. 2 is schematic view of a the medical system according to FIG. 1 with the active substance chain in an inserted position.

In order to overcome this disadvantage, a pulling device 20 is described in the scope of the invention, which is used as part of the medical system 10 to pull the active substance chain 50 from the wound. In order to pull the active substance chain 50 from a wound, the active substance chain 50 must be transformed from the free position 100 shown in FIG. 1 into the inserted position 110 shown in FIG. 2. In the free position 100, the active substance chain 50 is arranged separated from the pulling device 20. In contrast, in the inserted position 110 at least one of the storage units 51 is arranged with a positive fit in a recess 41, 41' of the pulling device 20.

The pulling device 20 has a grip element 30 and a coupling element 40. In the illustrated embodiment, the grip element 30 and the coupling element 40 are arranged like a T relative to each other. In the coupling element 40, two recesses 41, 41' are arranged. The storage units 51 can be laid in these recesses 41, 41'. Because the storage units 51 have, in general, a sphere-like shape, the recess 41, 41' is shaped like a cylinder, preferably by a blind borehole. This construction has the advantage that, when the active substance chain is pulled out of the wound, the storage units 51 are arranged with a positive fit in the recesses 41, 41'. Thus, the surface area by which the force is transmitted from the pulling device 20 into the active substance chain 50 is large. Thus, a diameter 43 of the recess should also be only slightly larger than the diameter of the storage unit 51. It is thereby ensured that large areas of the storage units 51 contact the walls of the recesses 41, 41'.

Figure 3:
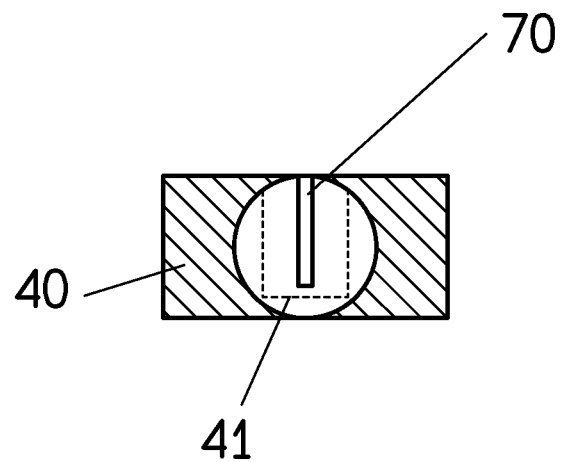
FIG. 3 is a schematic sectional view through the pulling device of FIG. 1 along the section line III-III.

In FIG. 3 a principal sectional view is shown through the pulling device 20 along the section line III-III from FIG. 1. The recess 41 has a cylindrical construction and is formed in the coupling element 40. In order to store the cord-like element 52 of the active substance chain 50, each of the two recesses 41, 41' is provided with a connection element 70. This connection element can connect two recesses 41, 41' at least partially to each other or can connect a recess 41 to an end region of the coupling element. Here, in an inserted position, the connection element 70 stores the cord-like element 52. Consequently, the cord-like element 52 can project from the coupling element 40 or can be guided through this element in the inserted position 110.

Figure 4:
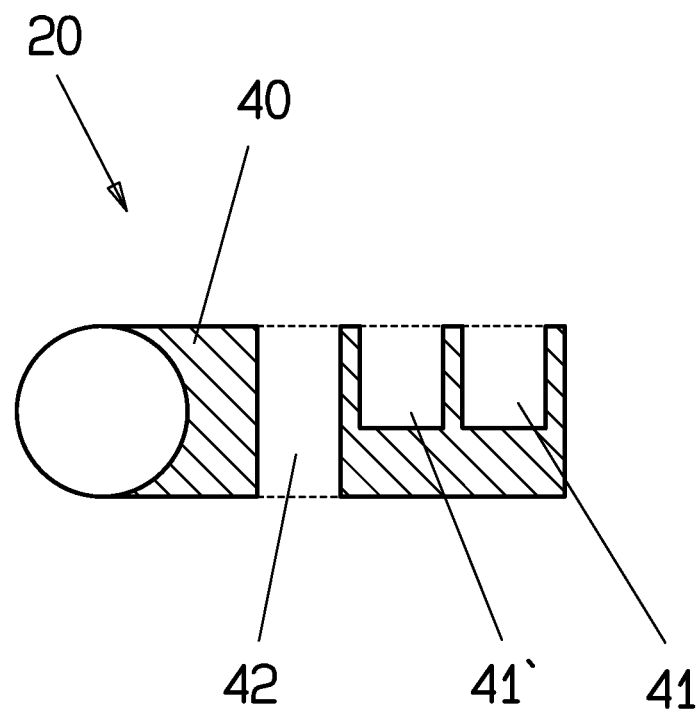
FIG. 4 is a schematic sectional view through the pulling device of FIG. 1 along the section line IV-IV.

FIG. 4 shows a passage element 42 that is likewise arranged in the coupling element 40. In contrast to the recesses 41, 41', the passage element 42 forms a passage in the coupling element 40. Consequently, an active substance chain 50 can be threaded through the passage element 42. According to the invention, it is now provided that the active substance chain 50 is to be pulled out of a wound by the pulling device 20. If this is pulled out partially, a user can bend the pulling device 20 according to the invention, in order to guide the storage units 51 out of the recesses 41, 41'. Then it is possible to move the active substance chain 50 through the passage element 42 and move the pulling device 20 in the direction of the wound. Then, by tilting the pulling device 20, the active substance chain 50 can be moved from the free position 100 back into the inserted position 110. The part of the active substance chain 50 that has already been pulled out is held in position by the passage element 42 and does not lead to an inadvertent movement of the active substance chain from the inserted position into the free position. In this way, the safety of the medical system 10 according to the invention is further increased.

Figure 5:
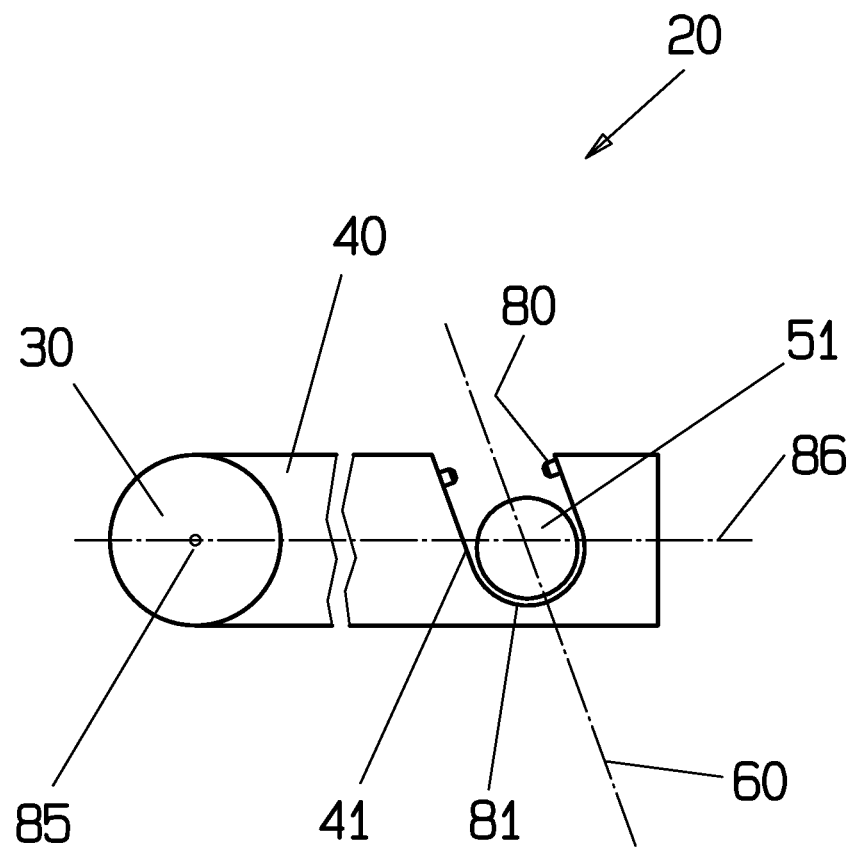
FIG. 5 is a schematic side view of a pulling device according to another embodiment of the invention.

In FIG. 5 is shown another advantageous construction of the pulling device 10 according to an embodiment of the invention. In the illustrated embodiment, the coupling element 40 has a recess 41, whose central axis 60 is inclined relative to a plane spanned by the grip element 30 and the coupling element 40. For clarification, a longitudinal axis 85 of the grip element 30 and a longitudinal axis 86 of the coupling element 40 are shown in the illustrated embodiment. These two axes span a plane relative to which the central axis 60 of the recess 41 is inclined. This inclination leads to the result that, for a forceful pulling of the active substance chain 50, the storage unit 51—here shown schematically—is pulled in the direction of a base region 81 of the recess 41, 41'. This leads to a self-locking of the active substance chain 50 in the pulling device 20 according to this embodiment of the invention.

Furthermore, the pulling device 20 has a collar-like retainer 80, which is arranged in an entry region of the recess 41. The collar-like retainer 80 provides for a fixing of the storage unit 51 in the recess 41. In order to improve the form-fit connection between the storage unit 51 and the recess 41, the base region 81 has a hemispherical construction in the shown embodiment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical system (10) comprising a pulling device (20) and an active substance chain (50), wherein:
   the active substance chain (50) has at least two storage units (51) arranged like a chain,
   at least one of the storage units (51) is loaded with a medicinal active substance,
   the pulling device (20) comprises a grip element (30) and a coupling element (40), the coupling element (40) having a first end attached to the grip element (30) and an opposing second free end, a longitudinal axis of the coupling element (40) extending from the first end to the second free end, and the coupling element (40) has at least two recesses (41, 41') therein, the two recesses (41, 41') being arranged linearly and co-axial to the longitudinal axis of the coupling element (40),
   in a free position (100) the active substance chain (50) is arranged separated from the pulling device (20),
   in an inserted position (110) at least one of the at least two storage units (51) is arranged form-fitting in one of the at least two recesses (41, 41'), and
   the active substance chain (50) is reversibly movable from the free position (100) into the inserted position (110),
   wherein the storage units (51) are connected by a cord-shaped element (52), the coupling element (40) has at least one generally slot-shaped connection element (70), and the connection element surrounds substantially an entire periphery of and stores the cord-shaped element (52) in the inserted position (110).

2. The medical system (10) according to claim 1, wherein each recess (41, 41') has a generally cylindrical shape.

3. The medical system (10) according to claim 1, wherein a diameter of each recess (41, 41') is greater than a diameter of a storage unit (51).

4. The medical system (10) according to claim 1, wherein the coupling element (40) has a passage element (42) forming a passage in the coupling element (40).

5. The medical system (10) according to claim 4, wherein the passage element (42) has a diameter greater than a diameter of each recess (41, 41').

6. The medical system (10) according to claim 1, wherein in an entry region of at least one of the recesses (41, 41') a collar-shaped retainer is arranged to fix the storage units (51) in the inserted position (110).

7. The medical system (10) according to claim 1, wherein a base region of at least one of the recesses (41, 41') has a generally hemispherical construction.

8. The medical system (10) according to claim 4, wherein the passage element (42) is arranged between at least one of the recesses (41, 41') and the grip element (30).

9. The medical system (10) according to claim 1, wherein the connection element at least partially connects two of the recesses (41, 41') to each other.

10. The medical system (10) according to claim 1, wherein the grip element (30) and the coupling element (40) are formed as one piece.

11. The medical system (10) according to claim 1, wherein the grip element (30) and the coupling element (40) are integral and/or materially uniform.

12. The medical system (10) according to claim 1, wherein the grip element (30) and the coupling element (40) are arranged as a T relative to each other.

13. A method for removing from a wound cavity an active substance chain (50) loaded with medicinal active substance, the method comprising engaging the active substance chain in at least one of the recesses (41, 41') of the coupling element (40) of the pulling device (20) according to claim 1 to form the inserted position (110), and pulling on the grip element (30) of the pulling device (20).

14. The method according to claim 13, wherein in an entry region of at least one of the recesses (41, 41'), a collar-shaped retainer is arranged to fix the storage units (51) in the inserted position (110).

15. The method according to claim 13, wherein the grip element (30) and the coupling element (40) are arranged as a T relative to each other.

16. The medical system (10) according to claim 4, wherein the connection element at least partially connects two of the recesses (41, 41') to each other and/or the connection element at least partially connects the passage element (42) and at least one of the recesses (41, 41') to each other.

17. A medical system (10) comprising a pulling device (20) and an active substance chain (50), wherein:
- the active substance chain (50) has at least two storage units (51) arranged like a chain,
- at least one of the storage units (51) is loaded with a medicinal active substance,
- the pulling device (20) comprises a grip element (30) and a coupling element (40), the grip element (30) having a first end, an opposing second end, and a midportion therebetween, a longitudinal axis of the grip element (30) extending from the first end to the second end thereof, the coupling element (40) having a first end and an opposing second free end, the first end of the coupling element (40) being fixedly attached to the midportion of the grip element (30), a longitudinal axis of the coupling element (40) extending from the first end to the second free end thereof, and the coupling element (40) has at least one recess (41, 41'),
- in a free position (100) the active substance chain (50) is arranged separated from the pulling device (20),
- in an inserted position (110) at least one of the storage units (51) is arranged form-fitting in the at least one recess (41, 41') such that the at least one recess surrounds substantially an entire periphery of the storage unit (51), and
- the active substance chain (50) is reversibly movable from the free position (100) into the inserted position (110),
- wherein the grip element (30) and the coupling element (40) are formed as one piece and are arranged as a T relative to each other such that the longitudinal axis of the coupling element (40) extends perpendicularly to the longitudinal axis of the grip element (30),
- wherein the storage units (51) are connected by a cord-shaped element (52), wherein the coupling element (40) has at least one generally slot-shaped connection element (70), and wherein the connection element surrounds substantially an entire periphery of and stores the cord-shaped element (52) in the inserted position.

* * * * *